(12) United States Patent
Hamper et al.

(10) Patent No.: US 9,115,315 B2
(45) Date of Patent: Aug. 25, 2015

(54) PETROCHEMICAL PROCESSES

(75) Inventors: Simon Hamper, Lake Jackson, TX (US); James R. Butler, League City, TX (US)

(73) Assignee: FINA TECHNOLOGY, INC., Houston, TX (US)

( * ) Notice: Subject to any disclaimer, the term of this patent is extended or adjusted under 35 U.S.C. 154(b) by 904 days.

(21) Appl. No.: 12/968,989

(22) Filed: Dec. 15, 2010

(65) Prior Publication Data

US 2011/0083998 A1    Apr. 14, 2011

(51) Int. Cl.
*C10G 55/06* (2006.01)
*C10G 35/04* (2006.01)
*C10G 63/04* (2006.01)

(52) U.S. Cl.
CPC ............... *C10G 35/04* (2013.01); *C10G 63/04* (2013.01)

(58) Field of Classification Search
USPC ............. 208/58, 65, 67, 69, 70, 79, 133, 137; 585/302, 304, 310, 650, 802
See application file for complete search history.

(56) References Cited

U.S. PATENT DOCUMENTS

| 3,714,033 | A |   | 1/1973 | Somekh et al. |
| 4,104,320 | A |   | 8/1978 | Bernard et al. |
| 4,440,627 | A | * | 4/1984 | Markley ........................ 208/65 |
| 4,594,145 | A |   | 6/1986 | Roarty |
| 4,595,668 | A |   | 6/1986 | Poeppelmeier et al. |
| 4,636,298 | A |   | 1/1987 | Buss et al. |
| 4,645,586 | A |   | 2/1987 | Buss |
| 5,100,534 | A | * | 3/1992 | Le et al. ........................ 208/70 |
| 6,407,301 | B1 | * | 6/2002 | Foley et al. ................... 585/650 |

* cited by examiner

*Primary Examiner* — Michelle Stein

(57) ABSTRACT

Petrochemical processes, including reforming processes are described herein. The reforming processes generally include introducing an input stream to a reforming unit having a reforming catalyst disposed therein, wherein the input stream includes a naphtha having an N+2A value of from about 65 to about 85 and contacting the input stream with the reforming catalyst and hydrogen to form an output stream.

8 Claims, 1 Drawing Sheet

PETROCHEMICAL PROCESSES

CROSS-REFERENCE TO RELATED APPLICATIONS

This application claims the benefit of U.S. patent application Ser. No. 11/411,706, filed Apr. 26, 2006.

FIELD

Embodiments of the present invention generally relate to petrochemical processes, such as reforming processes. In particular, embodiments of the invention relate to feedstocks for reforming processes.

BACKGROUND

Reforming processes generally include supplying straight run feedstocks, such as naphtha, to the reformer to form output streams having an increased octane number. However, the final octane number of the output stream, such as the octane number of gasoline and the value thereof, are determined by the N+2A value of the input stream.

Therefore, a need exists to provide a process of increasing the final octane number of reformer output streams.

SUMMARY

Embodiments of the present invention include reforming processes. The reforming processes generally include introducing an input stream to a reforming unit having a reforming catalyst disposed therein, wherein the input stream includes a naphtha having an N+2A of from about 65 to about 85 and contacting the input stream with the reforming catalyst and hydrogen to form an output stream.

Another embodiment generally includes a petrochemical process. The petrochemical process generally includes introducing a first input stream to a cracking unit, wherein the first input stream includes a naphtha feedstock, cracking the naphtha feedstock within the cracking unit to form a first output stream including light olefins and pygas, passing the pygas from the cracking unit to an extraction unit and separating benzene and toluene from the pygas within the extraction unit. The process further includes recovering a raffinate from the extraction unit, passing the raffinate from the extraction unit to a reforming unit having a reforming catalyst disposed therein, contacting the raffinate with the reforming catalyst to form a second output stream and recovering the second output stream from the reforming unit.

DETAILED DESCRIPTION

Introduction and Definitions

Figure 1:
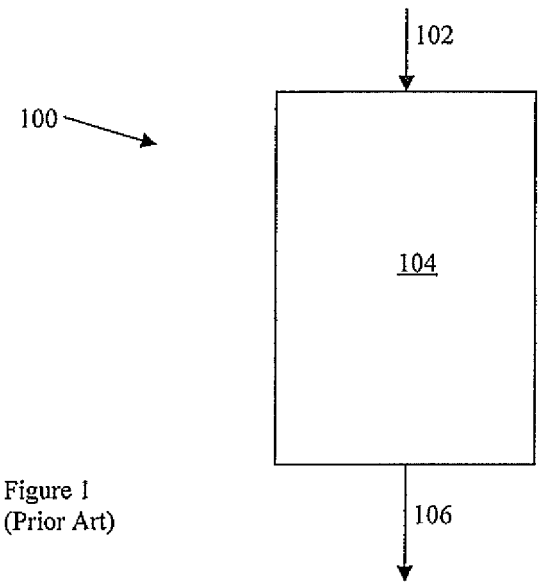
FIG. 1 illustrates a conventional reforming process.

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions when the information in this patent is combined with available information and technology.

Various terms as used herein are shown below. To the extent a term used in a claim is not defined below, it should be given the broadest definition persons in the pertinent art have given that term as reflected in printed publications and issued patents. Further, unless otherwise specified, all compounds described herein may be substituted or unsubstituted and the listing of compounds includes derivatives thereof.

Although not shown herein, the process stream flow may be modified based on unit optimization so long as the modification complies with the spirit of the invention, as defined by the claims. For example, at least a portion of any overhead fraction may be recycled as input to any other system within the process. Also, additional process equipment, such as heat exchangers, may be employed throughout the processes described herein and such placement is generally known to one skilled in the art.

Further, while described below in terms of primary components, the streams indicated below may include any additional components as known to one skilled in the art.

The term "regeneration" refers to a process for renewing catalyst activity and/or making a catalyst reusable after its activity has reached an unacceptable/inefficient level. Examples of such regeneration may include passing steam over a catalyst bed or burning off carbon residue, for example.

As used herein, the term "naphtha" refers to a cut in the range of $C_5$ to about 420° F. The term light virgin naphtha refers a naphtha cut in the range of $C_5$ to about 160° F., intermediate virgin naphtha refers to a naphtha cut in the range of from about 160° F. to about 280° F. and heavy virgin naphtha refers to a naphtha cut in the range of from about 280° F. to about 380° F. The term "virgin" refers to petroleum oils which have not been cracked or otherwise subjected to any treatment which would produce appreciable chemical change in their components.

The term "cut" refers to that portion of crude oil boiling within certain temperature limits. The limits may be on a crude assay true boiling point basis, for example.

The term "reforming" refers to the conversion of naphtha fractions to products of higher octane value.

The term "research octane number" refers to the percentage by volume of isooctane in a blend of isooctane and n-heptane that knocks with the same intensity as the fuel being tested.

The term "straight run feedstock" refers to an uncracked feedstock. The term "straight run gasoline" refers to an uncracked gasoline fraction distilled from crude oil.

FIG. 1 illustrates a conventional reforming process 100. The reforming process 100 generally includes providing an input stream 102 to a reformer unit 104 to form an output stream 106. Although illustrated in FIG. 1 as a single reformer unit 104, it is known in the art that the reforming process 100 may include a plurality of individual reformer units/stages.

The input stream 102 generally includes any hydrocarbon feedstock having a boiling point within the gasoline range. For example, the hydrocarbon feedstock may include light hydrocarbon oils boiling from about 70° F. to about 500° F. or from about 180° F. to about 400° F., for example.

Generally, the input stream 102 includes compounds selected from heavy straight run gasolines and heavy straight run naphthas (heavy virgin naphtha).

In addition, hydrogen is fed to the unit in any manner known to one skilled in the art. For example, hydrogen may be fed to and combined with the input stream 102 (e.g., input stream 102 includes hydrogen). The hydrogen may be added at a rate of from about 1,000 to about 8,000 scf/bbbl of input stream 102, for example.

The reformer unit 104 may include any vessel or number of vessels known to one skilled in the art, such as a fixed bed reaction vessel, for example. The reformer unit 104 may be operated at a reactor pressure of from about 30 psig to about 1000 psig or from about 30 psig to about 1000 psig, for example, a weight hourly space velocity (WHSV) of from about 0.5/hour to about 20/hour or from about 1/hour to about 10/hour and a hydrogen to input ratio of from about 1 to about 10 moles of hydrogen per mole of feed, for example.

The reformer unit 104 generally includes a reforming catalyst disposed therein. The reforming catalyst generally includes a metal component. The metal component may include a Group VIII noble metal, such as platinum.

The reforming catalyst may be supported or unsupported. When supported, the support material may include a refractory oxide (e.g., clay, alumina, silica or combinations thereof) or a zeolite, for example. The zeolite support may have an effective pore diameter of from about 6 angstroms to about 15 angstroms (e.g., zeolite-X, zeolite Y or zeolite-L), for example.

The reforming catalyst may further include a promoter. The promoter may include a metal selected from Groups IIA, IVA, IB, VIB, BIIB and BIII, such as gallium, tin, copper, chromium, rhenium, iridium and combinations thereof. The promoter may be present in an amount of from about 0.01 wt. % to about 5 wt. % or from about 0.1 wt. % to about 3 wt. % or from about 0.2 wt. % to 3 wt. %, for example.

Certain compounds present in either the input stream 102 or produced during the reaction, such as certain metals, hydrogen sulfide, ammonia, organic nitrogen and sulfur compounds, may deactivate the catalyst. Therefore, the reforming process 100 may further include a feed pretreater (not shown,) such as a hydrotreater to reduce the amount of these compounds present in the input stream 102.

However, reforming catalysts generally still experience deactivation. Therefore, the reforming process 100 may be continuous (e.g., on-line catalyst regeneration), cyclic (e.g., swing reactors) or semi-regenerative (e.g., off-line regeneration) depending upon the frequency of catalyst regeneration and other process considerations, for example.

Catalyst regeneration may include high temperature oxidation followed by chlorination, for example. See, U.S. Pat. No. 4,595,668, U.S. Pat. No. 4,645,586, U.S. Pat. No. 4,636,298, U.S. Pat. No. 4,594,145 and U.S. Pat. No. 4,104,320.

The input stream 102 generally contacts the reforming catalyst within the reformer unit 104 to form the output stream 106. The heavy straight run naphthas of the input stream 102 may have an N+2A value (naphthenes+2× aromatics) content of from about 30 to about 60 or from about 40 to about 55, for example. In addition, the output stream 106 generally includes a compound having an increased octane number than the input stream 102. However, the octane number is generally dependent upon the product produced and the intended use thereof.

The N+2A value of the input stream 102 generally provides limits on the octane number on the products within the output stream 106. For example, a higher N+2A value generally results in an increased $C_5$ and greater yield in the output stream 106. In addition, a higher N+2A value results in an increased ability to boost the octane number of the output and an increased liquid yield in the output stream 106, for example.

Figure 2:
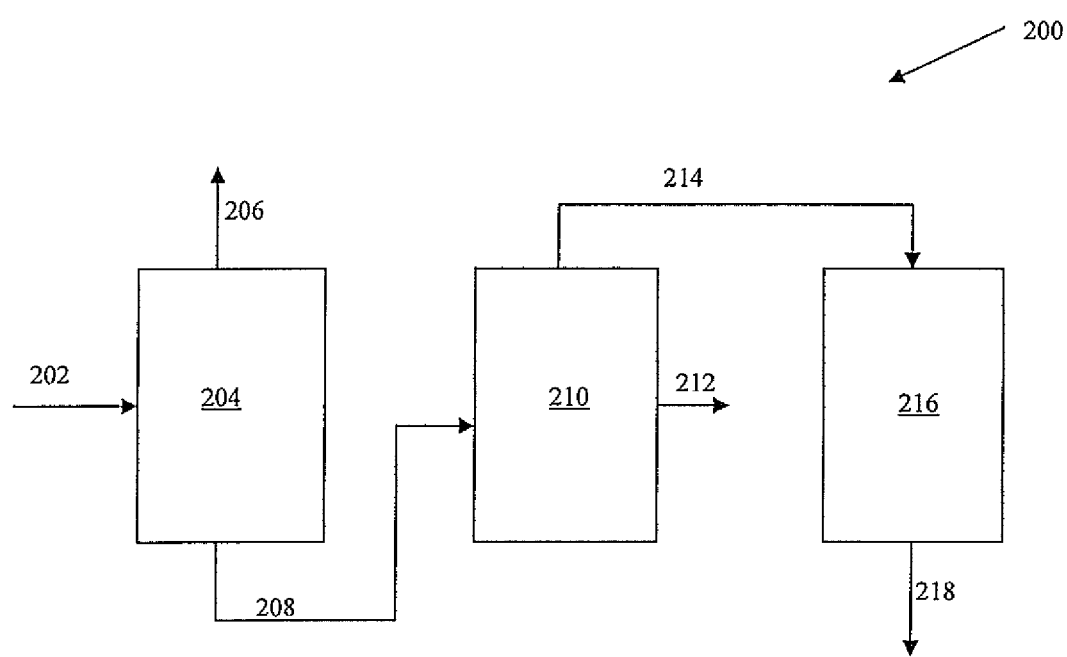
FIG. 2 illustrates a portion of a petrochemical process.

FIG. 2 illustrates a portion of a petrochemical process 200. The process 200 generally includes providing an input stream 202 to a naphtha cracker 204 to form an overhead fraction 206.

The input stream 202 generally includes a naphtha feedstock. The naphtha feedstock may include a mixture of paraffinic, naphthenic and aromatic hydrocarbons having varied molecular weight and molecular structure, for example.

In one embodiment, the input stream 202 includes virgin naphtha. The virgin naphtha may be supplied from any source. However, in one embodiment, the virgin naphtha is supplied from a former reformer feed source. For example, embodiments of the invention may include retrofitting an existing petrochemical process including a reforming unit, such as that illustrated in FIG. 1. Such retrofit may include rerouting the feed from the reforming unit to the naphtha cracker, for example. The aromatics content of the former reforming feed (N+2A of from about 40 to about 50) is contemplated to result in an increased conversion rate. The N+2A value of the former reforming feed may further provide more cracking feed to the naphtha cracker due to the higher paraffin level, for example.

The naphtha cracker 204 may include any vessel or number of vessels known to one skilled in the art for the production of light olefins, such as ethylene and/or propylene, for example. In one embodiment, the naphtha cracker 204 includes a steam cracker.

The overhead fraction 206 generally includes light olefins (e.g., ethylene and propylene.)

In addition to the overhead fraction 206, the naphtha cracking process generally produces pyrolysis gasoline as a by-product, which is recovered via line 208.

Pyrolysis gasoline (also referred to as "pygas") is a liquid by-product of the cracking process and is generally a gasoline (e.g., a highly unsaturated hydrocarbon mixture ($C_5$ to $C_{14}$) that is rich in dienes, olefin and aromatics) boiling in the temperature range of from about 97° F. to about 450° F., for example.

The pygas may be sent to an extraction unit 210 to separate benzene and/or toluene from other components present in the pyrolysis gasoline, for example. Although not shown in the figures, it is known to one skilled in the art that the pygas may undergo hydrogenation prior to extraction, for example. Such extraction processes are generally known to one skilled in the art. See, U.S. Pat. No. 3,714,033.

A BTX fraction may be recovered via line 212. The BTX fraction may include benzene, toluene, $C_8$ aromatics (ortho-xylene, meta-xylene, paraxylene and ethyl benzene), $C_9$ aromatics and combinations thereof, for example.

Raffinate may be recovered via line 214. The term "raffinate" refers to the residue recovered from an extraction process. Embodiments of the invention generally include utilizing the raffinate formed from such extraction as input for reforming units. It is contemplated that the raffinate aromatics content (N+2A of from about 75 to about 85) would result in more efficient boosting of the octane number of the reforming input stream. Therefore, embodiments of the invention generally include passing the raffinate via line 214 to a reformer unit 216 to form a reformer output 218.

While the foregoing is directed to embodiments of the present invention, other and further embodiments of the invention may be devised without departing from the basic scope thereof and the scope thereof is determined by the claims that follow.

What is claimed is:

1. A petrochemical process comprising: introducing a first input stream to a cracking unit, wherein the first input stream comprises a virgin naphtha feedstock, wherein said virgin naphtha feedstock is a former reformer input stream;
   cracking the virgin naphtha feedstock within the cracking unit to form a first output stream comprising light olefins and pygas;
   passing the pygas from the cracking unit to an extraction unit;
   separating benzene and toluene from the pygas within the extraction unit;
   recovering a raffinate from the extraction unit having a higher N+2A than the virgin naphtha feedstock;
   passing the raffinate from the extraction unit to a reforming unit having a reforming catalyst disposed therein;
   contacting the raffinate with the reforming catalyst to form a second output stream; and
   recovering the second output stream from the reforming unit.

2. The process of claim 1, wherein the virgin naphtha feedstock comprises a N+2A value of from about 40 to about 55.

3. The process of claim 1, wherein the cracking unit comprises a steam cracker.

4. The process of claim 1 further comprising hydrogenating the pygas prior to extraction.

5. The process of claim 1, wherein the raffinate comprises a N+2A value of from about 75 to about 85.

6. The process of claim 1, wherein the reforming catalyst comprises a Group VIII noble metal.

7. The process of claim 1, wherein the reforming catalyst comprises a promoter selected from gallium, tin, copper, chromium, rhenium, iridium and combinations thereof.

8. The process of claim 1 further comprising supplying hydrogen to the reforming unit.

* * * * *